(12) United States Patent
Moreton

(10) Patent No.: US 8,247,237 B2
(45) Date of Patent: Aug. 21, 2012

(54) SILICA-BASED INDICATING DESICCANTS

(75) Inventor: Stephen Moreton, Warrington (GB)

(73) Assignee: PQ Silicas UK Limited, South Yorkshire (GB)

( * ) Notice: Subject to any disclaimer, the term of this patent is extended or adjusted under 35 U.S.C. 154(b) by 1946 days.

(21) Appl. No.: 10/549,670

(22) PCT Filed: Jan. 21, 2004

(86) PCT No.: PCT/GB2004/000250
§ 371 (c)(1),
(2), (4) Date: Jul. 3, 2006

(87) PCT Pub. No.: WO2004/083849
PCT Pub. Date: Sep. 30, 2004

(65) Prior Publication Data
US 2006/0258016 A1    Nov. 16, 2006

(30) Foreign Application Priority Data
Mar. 19, 2003 (GB) .................................. 0306278.3

(51) Int. Cl.
*G01N 21/75* (2006.01)
*G01N 33/18* (2006.01)
*G01N 31/00* (2006.01)
*G01N 33/00* (2006.01)

(52) U.S. Cl. ......................... 436/166; 436/39; 252/408.1

(58) Field of Classification Search ............... 436/177
See application file for complete search history.

(56) References Cited

U.S. PATENT DOCUMENTS

| | | | |
|---|---|---|---|
| 2,460,065 A | 1/1949 | Davis | |
| 2,460,067 A | 1/1949 | Davis | |
| 2,460,069 A | 1/1949 | Davis | |
| 2,460,070 A | 1/1949 | Davis | |
| 2,460,071 A | 1/1949 | Davis | |
| 2,460,072 A | 1/1949 | Davis | |
| 2,460,073 A | 1/1949 | Davis | |
| 2,460,074 A | 1/1949 | Davis | |
| 3,898,172 A | 8/1975 | Reif et al. | |
| 6,655,315 B1 * | 12/2003 | Gattiglia | .............. 116/206 |

FOREIGN PATENT DOCUMENTS

| | | |
|---|---|---|
| CN | 1269507 | 5/2001 |
| DE | 1952539 | 4/1971 |
| GB | 280934 | 2/1929 |
| GB | 345672 | 3/1931 |
| JP | Hei 7-17582 | 1/1995 |
| KR | 2002015163 A | 2/2002 |
| RU | 989479 | 1/1983 |
| WO | WO 98/16821 | 4/1998 |
| WO | WO 00/65339 | 11/2000 |
| WO | WO 01/09601 | 2/2001 |
| WO | WO 02/57772 | 7/2002 |

OTHER PUBLICATIONS

Belotserkovskaya et al. "Indicator properties of vanadium-modified silicas and zeolites." *Zh. Prikl. Khim.* 63:8 (1990) 1674-9 (English abstract only).

Malygin et al. "Synthesis and study of physiochemical properties of vanadium-containing silica—a humidity indicator." *Sb. Nauch. Tr. VNII Lyuminoforov I Osobo Christ. Veshchestv* 23 (1982) 24-8 (English abstract only).

Malygin et al. "Study of properties of vanadium-containing silica gel." *Zh. Prikl. Khim.* 52:9 (1979) 2094-6 (English abstract only).

International Search Report, dated May 25, 2004, for PCT/GB2004/000250.

Japanese Official Action for JP2006-505884 with English Translation.

English Translation for Japanese Patent Kokai Hei 7-17582 Dai Nippon Printing Co., Ltd. dated Jan. 20, 1995.

\* cited by examiner

*Primary Examiner* — Jill Warden
*Assistant Examiner* — Bryan Kilpatrick
(74) *Attorney, Agent, or Firm* — Buchanan Ingersoll & Rooney PC

(57) ABSTRACT

An indicating desiccant comprises a silica-based material having impregnated thereon a source of iron and a source of bromide, the source of iron being present in an amount up to 2.0 percent by weight, calculated as Fe with respect to weight of the silica-based material, and the source of bromide being present in an amount such that the weight ratio of Br to Fe is at least 0.1:1.

33 Claims, No Drawings

SILICA-BASED INDICATING DESICCANTS

CROSS REFERENCE TO RELATED APPLICATION

This application is the National Phase application of International Application No. PCT/GB2004/000250, filed 21 Jan. 2004, which designates the United States and was published in English. This application, in its entirety, is incorporated herein by reference.

This invention relates to silica-based indicating desiccants.

Cobalt chloride indicator silica gels are used in a range of applications, e.g. to indicate moisture uptake in gas drying columns. Other drying applications include their use in transformer breathers, tank breathers, in the protection of electronics and telecommunication systems and in laboratory desiccators. It is estimated that approximately 4000 tonnes of cobalt chloride indicator gel are used annually on a global basis.

Cobalt-containing gels for use as humidity indicators have been disclosed in U.S. Pat. No. 2,460,071 (disclosing cobalt chloride), U.S. Pat. No. 2,460,069 (disclosing cobalt bromide), U.S. Pat. No. 2,460,073 (disclosing cobalt iodide), U.S. Pat. No. 2,460,074 (disclosing cobalt thiocyanate), U.S. Pat. No. 2,460,065 (disclosing cobalt sulphate) and U.S. Pat. No. 2,460,070 (disclosing cobalt phosphate).

Indicator silica gel is currently produced by impregnating humidified silica gel or a silica hydrogel with a cobalt chloride solution to produce a dry, granular end-product which contains a minimum of 0.5% cobalt chloride and which is blue in colour, changing to pink when water has been adsorbed. Humidified gel is silica gel that has been saturated with water from the vapour phase in order to avoid decrepitation or disintegration upon impregnation. If the cobalt chloride solution is added directly to the dried gel, the grain size is reduced.

The hazard classification of cobalt chloride according to European legislation was recently amended (notification from the EEC, Dec. 15, 1998) with the consequence that the use of cobalt chloride indicator gel in industrial applications now requires much tighter control to ensure exposure limits are strictly controlled. If acceptable alternatives to the cobalt chloride indicator gel were not available to indicate when saturation has occurred in gas/air drying applications, for instance, this could have serious implications on the users' downstream processes, e.g. corrosion through moisture damage.

It has been demonstrated that the vanadium compound $VOCl_3$, when impregnated into silica gel gives a colour change from colourless to yellow to orange to red to brown as humidity increases according to the following references:

Belotserkovskaya et al., "Indicator properties of vanadium-modified silicas and zeolites" Zh. Prikl. Khim. (Leningrad), 63(8), 1674-9;

Malygin, A. A. "Synthesis and study of physicochemical properties of vanadium-containing silica—a humidity indicator", Sb. Nauch. Tr. VNII Lyuminoforov I Osobo Chist. Veshchestv, 23, 24-8; and Malygin, A. A. et al, "Study of properties of vanadium-containing silica gel", Zh. Prikl. Khim. (Leningrad), 52(9), 2094-6.

However, $VOCl_3$ is corrosive, toxic and difficult to prepare and handle.

U.S. Pat. No. 2,460,072 and U.S. Pat. No. 2,460,067 disclose the use of copper(II) chloride and copper(II) bromide, respectively, but the amounts of these used in these patents means that the silica-based products described therein are not considered suitable candidates for a commercial silica-based humidity indicator because of potential toxicity and environmental considerations.

A system based on copper chloride to which is added additional chloride in the form of a soluble chloride, such as magnesium chloride, has been disclosed in International patent application WO 01/09601 A1. Another system, in which soluble bromide salts are added to copper salts and impregnated into silica gel has also been disclosed (International patent application WO 2002/57772 A). These change colour in the region of 20% relative humidity (R.H.), which is similar to the humidity at which the cobalt chloride system undergoes its colour change.

Another system changing colour at similar, or slightly higher (20-30%), humidity is based on iron(III) salts, in particular ammonium iron(III) sulphate (International patent application WO 00/65339). Other systems have recently been disclosed employing pH indicators incorporated into the gel (Korean patent application 2002015163 A and Chinese patent application 1269507 A). However these organic systems suffer from various drawbacks. All are thermally unstable, thus limiting the number of times they can be regenerated by heating. Some contain sulphuric acid to adjust the pH. This has implications for corrosion of metal in contact with them. Some are photosensitive and fade in bright light.

The current systems generally change colour at relative humidities around, or in excess of, 20% relative humidity. For many applications this is ideal. It is not, however, appropriate for applications where a colour change at a lower humidity is required. Examples of this may include breathers for transformer units where even very low levels of moisture cannot be tolerated.

There is a need for a system which has a pronounced colour change at a low relative humidity (below 20% R.H., for example 15% R.H. or lower). The iron-based system above cannot achieve this. It is unclear if the organic systems can but they have drawbacks as described above. The copper systems can be made to change colour at the low humidity required but in order to do so, and still to have a distinct colour change, they must contain relatively high (e.g. approximately 0.1% or more) levels of copper. At such levels the toxicity of the copper becomes an issue. Lower levels of copper either do not result in a colour change at the desired humidity, or their colours are indistinct. An additional problem with such systems is their temperature sensitivity. It has been found that those copper-based systems which do change at the required humidity are very sensitive to the temperature at which they are dried. Drying temperatures differing by only a few tens of degrees result in gels of very different colours ranging from pale greenish to deep olive green/brown shades. Such variations would create difficulties in manufacturing and in regeneration. Trying to stabilise the colour by adding more halide only shifts the % R.H. of the colour change to too high a value.

This invention seeks to provide a humidity indication system which is capable of producing a distinct colour change at a low percent relative humidity and may be substantially entirely copper-free.

According to the invention, an indicating desiccant comprises a silica-based material which is provided with, e.g. impregnated with, a source of iron and a source of bromide.

The iron and bromide constituents constitute the primary active indicator system of the desiccant.

The source of iron is typically present in an amount of from 0.01 percent up to 2.0 percent by weight, calculated as Fe with respect to weight of the anhydrous silica-based material.

The source of bromide may be present in an amount such that the weight ratio of Br to Fe is at least 0.1:1.

The desiccant of the invention will usually be essentially copper free; however, the possible presence is not excluded of, for example, trace impurity levels of copper or even copper introduced deliberately into the system at levels less than 0.002 percent by weight with respect to the anhydrous silica-based material.

The silica-based material can be any material capable of acting as a desiccant. Typically, a silica gel is used as the material, but other forms of silica may be used. The silica-based material may have any of the physical forms normally available. In particular, the form can be irregular granules or approximately spherical beads (often called spherical or beaded silica gel).

A particularly useful silica gel has a pore volume to nitrogen between 0.2 and 2.0 $cm^3g^{-1}$ and a BET surface area in the range 200 to 1500 $m^2g^{-1}$. Usually, the average particle size of such a silica gel will be in the range 0.1 to 8 mm.

The source of iron is usually an iron(III) salt. Typical salts include iron(III) sulphate, iron(III) chloride, and iron(III) nitrate. Best results have been obtained using the double sulphates, or alums, ammonium iron(III) sulphate and potassium iron(III) sulphate. Alternatively the iron may be introduced in the iron(II) state, for example, as ammonium iron(II) sulphate, in which case it will oxidise to the iron(III) state during the impregnation and drying stages. The amount of the source of iron, calculated as Fe, is up to 2.0 percent by weight of the anhydrous silica-based material, but excellent indicating desiccants can be produced using much lower amounts of Fe. Preferably, the amount of Fe is in the range 0.02 to 1.0 percent by weight, more preferably in the range 0.05 to 0.3 percent by weight with respect to the anhydrous silica-based material.

The source of bromide can be any material which acts as a source of the bromide ion in the silica-based material. Any water-soluble bromide can be used and typical sources of bromide include alkali metal bromides, alkaline earth metal bromides, transition metal bromides and ammonium bromide. Preferred sources of bromide are sodium bromide, potassium bromide, calcium bromide, magnesium bromide, zinc bromide and ammonium bromide.

The amount of the source of bromide present may be related to amount of the source of iron present. The ratio of Br to Fe may be at least 0.1:1 by weight and up to 100:1 by weight. More usually, the ratio of Br to Fe is in the range 0.5:1 to 50:1 by weight and commonly the ratio is in the range 1:1 to 20:1. Usually, though not always, the amount of bromide is equal to, or greater than, the amount of iron.

A desiccant in accordance with the invention may be tailored to produce a marked colour change when the amount of water adsorbed is such that the equilibrium relative humidity is in the range 5 to 15 percent, in order to indicate the need to the user to replenish or reactivate the silica gel. For some desiccant applications a different equilibrium relative humidity may be preferred, in which case other ratios of Br to Fe may be more appropriate to produce a colour change at a different relative humidity.

The indicating desiccant of the invention typically demonstrates a colour change from deep amber/brown in the absence of moisture to pale yellow when in equilibrium with an atmosphere with a relative humidity of about 10% or more. The colour of the anhydrous desiccant may be affected by the amount of source of iron present and the ratio of Br to Fe. The presence of the bromide has the surprising effect of intensifying the initial, dry colour, of the indicating desiccant when compared to a desiccant containing the same quantity of iron but no bromide. The presence of bromide also has the surprising effect of moving the point at which the colour change occurs to a lower percent relative humidity when compared to an indicating desiccant containing the same quantity of iron but no bromide.

A method of preparing an indicating desiccant according to the invention comprises impregnating a silica-based material with a source of iron and a source of bromide, thereby introducing into the silica-based material the source of iron in an amount up to 2.0 percent by weight, calculated as Fe with respect to weight of the anhydrous silica-based material, and the source of bromide in an amount such that the weight ratio of Br to Fe is at least 0.1:1.

In a typical process, the indicating desiccant silica-based material, e.g. silica gel, is prepared by contacting the silica-based material with a solution of an iron(III) salt containing from 0.05 percent of the salt by weight up to the saturation concentration of the iron salt, e.g. by soaking a humidified white silica gel in the iron salt solution. Humidified gel (i.e. previously dried silica gel which has been contacted with a source of moisture, such as steam, until the water content is approximately 20 to 30 percent by weight) is preferred, but the use of dry gel or a hydrogel is acceptable. When dry gel is used, the granules decrepitate, so that the product has a smaller particle size than the original product, but, generally, the particle size is still satisfactory for use as a desiccant agent.

For a typical iron salt such as ammonium iron(III) sulphate, the solution used may range from 0.1 percent by weight to approximately 40 percent by weight (saturation at 25° C.), or higher if higher temperatures are used. Preferably, the solution contains 1 to 20 percent by weight of the iron salt, e.g. ammonium iron(III) sulphate, at 25° C. The use of a higher concentration of iron salt helps to reduce the processing time for preparing the indicating silica-based desiccant.

Usually, the solution containing the source of iron used for impregnating the silica-based material also contains the source of bromide. The solubility of suitable sources of bromide, such as sodium bromide, is normally such that there is no problem obtaining a sufficiently concentrated solution and the concentration of the source of bromide in the solution will be determined by the desired ratio of bromide to iron to be achieved.

In a typical process, the silica-based material is soaked in the solution for a period of from 10 minutes to 10 days, e.g. from 1 to 30 hours, and typically from 2 to 12 hours. The excess solution is drained and the gel may be dried at 80° C. to 230° C. whereupon it develops its deep amber or brown colour.

An impregnated product dried in this manner will usually have a weight loss after heating at 145° C. for 16 hours of less than 10 percent by weight. Preferably, the weight loss at 145° C. is less than 2 percent by weight.

Alternatively, the silica-based material can be impregnated by mixing with a small amount of a concentrated solution of the impregnants, as described in U.S. Pat. No. 2,460,067. Typically, a silica-based material such as silica gel is humidified to about 15 to 30 percent moisture and then impregnated with a relatively concentrated solution of an iron(III) salt and a source of bromide, the amount of solution used being just sufficient to produce the required loading on the silica. For example, using this method, a loading of about 0.27 percent Fe by weight and 1.8 percent bromide by weight based on silica-based material can be produced by adding about 14 g of a solution containing 2.0 g ammonium iron(III) sulphate 12-hydrate and 2.0 grams sodium bromide to 100 g of humidified silica gel (containing 17.2% water). The silica gel produced contains a ratio of Br to Fe of approximately 7:1.

It is sometimes convenient to impregnate the silica gel with separate solutions of the impregnants in sequence. After the silica gel has been mixed with the solution or solutions it is dried as previously described, typically in the range 80° C. to 230° C.

The second technique may, compared with the method wherein the silica gel is soaked in a solution, be advantageous because the additive levels are easier to control. The source of iron and source of bromide are not necessarily absorbed from a common solution in the proportion in which they are present in the solution. Therefore, after a batch of silica gel has been impregnated by soaking, it is usually necessary to adjust the concentrations of the iron source and the bromide source in the soaking solution before it can be used again. This is not a problem with the alternative method using a small amount of relatively concentrated solution.

Silica-based indicating desiccants which have been prepared in accordance with the invention have been found to show a strong colour change when they approach equilibrium with relative humidities of around 10-20%, from deep amber or brown to pale yellow. The colour change is reversible when the desiccant is dried and the desiccant can be therefore be regenerated at least once, and often many times, for further use.

In contrast to the copper bromide desiccants described in U.S. Pat. No. 2,460,067, and some of those in the other copper-based systems described above, the colour of the dry material and the relative humidity at which a colour change occurs have been found to be hardly affected by the temperature at which the material is dried. Where an alternative colour is preferred, this can readily be produced by adjustment of the amounts of iron and bromide and the ratio of these components. The relative humidity at which a colour change occurs can also be varied by varying the amount and ratios of these components.

The invention is illustrated by the following non-limiting examples.

EXAMPLES

In the following examples "humidified silica gel" means Sorbsil silica gel, of particle size 2.5 to 6.0 mm, available from INEOS Silicas Limited (formerly Crosfield Limited), which has been exposed to humid air, or steam, until the pore structure contains water to an extent greater than 70% of its capacity to hold water. Typically, such gel contains 22 to 27% water by weight.

The colour changes associated with the indicating gels were determined by placing samples (typically about 9 to 13 grams) into a series of glass tubes and passing air at various relative humidities through the samples for 7 hours at a flow rate of 4 liters/minute. The colours of the products were measured using a Minolta CR200 Chromameter, calibrated to a standard white plate using CIE Illuminant C and an observer angle of 2°. Results were expressed using the L*a*b* system in which L* represents the lightness (the higher the value the lighter the shade), a* the red/green component (positive values are red, negative values are green) and b* the yellow/blue component (positive values are yellow, negative values are blue).

Example 1

100 gram quantities of humidified silica gel were soaked in 200 mls of solutions containing various amounts of ammonium iron(III) sulphate 12 hydrate (iron alum) and magnesium bromide hexahydrate for four hours with gentle stirring at hourly intervals. The solution was then decanted and the gel drained and then dried at 145° C. for 16 hours. The dried gel was analysed for its content of iron and bromide and its colours measured after exposure to a range of relative humidities.

Compositions are given in Table 1.

TABLE 1

| Composition | Solution composition | | Composition of dry gel | | Weight ratio |
|---|---|---|---|---|---|
| | % iron alum | % MgBr2.6H2O | % Fe | % Br | Br:Fe |
| 1a | 1 | 0 | 0.06 | 0 | 0 |
| 1b | 1 | 10 | 0.05 | 0.85 | 17 |
| 1c | 1 | 20 | 0.07 | 1.70 | 24.3 |
| 1d | 3 | 0 | 0.09 | 0 | 0 |
| 1e | 3 | 3 | 0.10 | 0.32 | 3.2 |
| 1f | 3 | 20 | 0.13 | 2.04 | 15.7 |
| 1g | 5 | 0 | 0.16 | 0 | 0 |
| 1h | 5 | 3 | 0.17 | 0.40 | 2.4 |
| 1i | 5 | 20 | 0.14 | 2.05 | 14.6 |
| 1j | 10 | 0 | 0.20 | 0 | 0 |
| 1k | 10 | 10 | 0.18 | 1.42 | 7.9 |
| 1l | 10 | 20 | 0.23 | 2.57 | 11.2 |

The indicating gels mentioned in Table 1 were exposed to streams of air at various relative humidities (% R.H.), as described above, and the resulting colours measured and recorded below in Table 2.

TABLE 2

| Composition | % R.H. | L* | a* | b* | Colour |
|---|---|---|---|---|---|
| 1a | 0 | 47.94 | +4.36 | +27.98 | Orange |
| | 10 | 48.34 | +4.49 | +26.71 | Orange |
| | 20 | 53.10 | +2.73 | +24.52 | Light orange |
| | 40 | 52.41 | +1.48 | +18.82 | Pale orange |
| | 80 | 61.14 | +0.07 | +13.96 | Pale yellow |
| 1b | 0 | 41.04 | +19.58 | +52.06 | Deep orange |
| | 10 | 55.41 | −2.61 | +15.32 | Pale yellow |
| | 20 | 57.41 | −2.18 | +13.59 | Pale yellow |
| | 40 | 62.84 | −0.91 | +3.97 | Almost colourless |
| | 80 | 65.76 | −1.25 | +6.88 | Almost colourless |
| 1c | 0 | 37.07 | +19.92 | +42.39 | Deep orange |
| | 10 | 56.74 | −3.73 | +21.68 | Pale yellow |
| | 20 | 60.79 | −1.50 | +9.56 | Very pale yellow |
| | 40 | 63.83 | −0.52 | +4.70 | Almost colourless |
| | 80 | 63.80 | −0.71 | +7.39 | Almost colourless |
| 1d | 0 | 47.40 | +5.44 | +32.56 | Orange |
| | 10 | 49.54 | +5.17 | +32.52 | Orange |
| | 20 | 50.57 | +3.85 | +31.64 | Light orange |
| | 40 | 55.66 | −0.52 | +12.21 | Pale yellow |
| | 80 | 61.47 | −0.66 | +4.66 | Almost colourless |
| 1e | 0 | 45.07 | +13.26 | +53.62 | Orange |
| | 10 | 46.38 | +4.43 | +35.32 | Light orange |
| | 20 | 57.72 | +1.54 | +31.80 | Pale orange |
| | 40 | 62.48 | −1.12 | +12.27 | Very pale orange |
| | 80 | 62.28 | −1.12 | +8.04 | Almost colourless |
| 1f | 0 | 31.02 | +21.53 | +35.23 | Deep orange/brown |
| | 10 | 44.91 | +2.29 | +41.48 | Yellow |
| | 20 | 55.67 | −1.79 | +20.92 | Yellow |
| | 40 | 58.10 | −0.75 | +10.71 | Very pale yellow |
| | 80 | 62.26 | −0.45 | +7.65 | Almost colourless |
| 1g | 0 | 51.47 | +6.48 | +35.34 | Orange |
| | 10 | 48.26 | +7.22 | +35.46 | Orange |
| | 20 | 47.43 | +5.75 | +31.28 | Light orange |
| | 40 | 56.88 | −0.14 | +16.74 | Pale yellow |
| | 80 | 63.02 | −0.97 | +8.55 | Almost colourless |
| 1h | 0 | 39.02 | +13.35 | +40.90 | Orange |
| | 10 | 43.74 | +7.59 | +37.28 | Light orange |
| | 20 | 55.31 | +2.16 | +33.03 | Light orange |
| | 40 | 64.22 | −1.72 | +13.76 | Pale yellow |
| | 80 | 70.03 | −1.90 | +10.36 | Almost colourless |
| 1i | 0 | 28.02 | +20.64 | +27.64 | Brown |
| | 10 | 42.17 | +7.37 | +39.30 | Yellow/orange |

TABLE 2-continued

| Composition | % R.H. | L* | a* | b* | Colour |
|---|---|---|---|---|---|
| | 20 | 49.36 | +2.34 | 32.86 | Pale orange |
| | 40 | 62.13 | +20.23 | +20.23 | Pale yellow |
| | 80 | 60.68 | −0.29 | +13.36 | Pale yellow |
| 1j | 0 | 46.19 | +9.20 | +41.14 | Orange |
| | 10 | 48.41 | +9.25 | +38.26 | Orange |
| | 20 | 50.12 | +5.96 | +37.94 | Light orange |
| | 40 | 51.38 | +1.57 | +25.68 | Pale orange |
| | 80 | 61.10 | −1.35 | +14.24 | Pale yellow |
| 1k | 0 | 26.91 | +17.63 | +21.98 | Deep amber/brown |
| | 10 | 32.78 | +17.16 | +31.36 | Amber |
| | 20 | 48.16 | +6.50 | +36.98 | Orange |
| | 40 | 53.99 | +1.37 | +30.38 | Light orange |
| | 80 | 63.56 | −2.83 | +19.49 | Pale yellow |
| 1l | 0 | 24.25 | +17.70 | +19.23 | Brown |
| | 10 | 32.80 | +16.06 | +32.52 | Amber |
| | 20 | 43.25 | +10.11 | +38.90 | Amber |
| | 40 | 54.96 | −0.97 | +21.96 | Yellow |
| | 80 | 60.91 | −1.63 | +18.86 | Light yellow |

Compositions 1a, 1d, 1g and 1j above contain no iron and so serve as controls for the others. These controls show a gradual fading of colour on passing from a dry state to a humid one. Those with bromide all have much deeper colours when dry compared to those without bromide, but all compositions, with or without bromide, become pale yellow or almost colourless when exposed to humidity. As they begin with a much deeper shade than the systems without bromide, but finish with a similar pale humidified colour, the overall colour change is much more dramatic in the gels containing bromide. The best parameter for following the colour change is the a* value (red/green component) as it is this which is the principal contributor to the initial amber colour. Plotting this against % relative humidity shows a sudden fall in a* in going from 0% R.H. to 10% to 20% R.H. for the systems containing bromide, but not for those without bromide. This effect is especially apparent in compositions 1e, 1f, 1h and 1i above. In these cases the fall in a* value is particularly sharp between 0 and 10% R.H., much less between 10 and 20%, thereafter it is very slight. Visually, this results in a dramatic colour change by the time the relative humidity has reached just 10%. This contrasts with the a* values for the controls which show only a modest, and steady decline in passing from 0 to 10% to 20% to 40% R.H.

Example 2

Weighed quantities of ammonium iron(III) sulphate 12-hydrate (iron alum) and magnesium bromide hexahydrate were dissolved in 5 cm³ water and mixed with 134 grams of humidified gel containing 24.5% water and then dried at 145° C. for 16 hours. The quantities were calculated to give 100 grams of indicating gel after drying containing similar levels of iron but different amounts of bromide. Compositions (percentages are by weight of the dry product) determined by analysis are shown in Table 3 below.

TABLE 3

| Composition | % Fe | % Br | Weight ratio Br:Fe |
|---|---|---|---|
| 2a | 0.15 | 0 | 0 |
| 2b | 0.18 | 0.49 | 2.7 |
| 2c | 0.16 | 0.96 | 6 |

The indicating gels in Table 3 were exposed to streams of air at various relative humidities (% R.H.), as described above, and the resulting colours measured and recorded below in Table 4.

TABLE 4

| Composition | % R.H. | L* | a* | b* | Colour |
|---|---|---|---|---|---|
| 2a | 0 | 63.08 | +6.46 | +49.76 | Light orange |
| | 10 | 67.56 | +2.65 | +50.06 | Yellow |
| | 20 | 70.70 | +2.14 | +42.08 | Yellow |
| | 40 | 75.15 | −0.08 | +22.30 | Pale yellow |
| | 80 | 80.10 | −1.66 | +9.35 | Almost colourless |
| 2b | 0 | 34.74 | +16.60 | +31.93 | Deep orange |
| | 10 | 48.30 | +0.90 | +36.50 | Yellow |
| | 20 | 53.77 | +0.93 | +33.18 | Yellow |
| | 40 | 57.66 | −1.64 | +19.84 | Yellow |
| | 80 | 66.23 | −2.52 | +12.62 | Pale yellow |
| 2c | 0 | 30.60 | +17.66 | +23.78 | Amber/brown |
| | 10 | 47.14 | +4.69 | +39.61 | Orange |
| | 20 | 52.89 | +3.18 | +37.47 | Orange |
| | 40 | 61.83 | −2.52 | +19.52 | Yellow |
| | 80 | 65.95 | −3.40 | +14.43 | Pale yellow |

As before, the compositions with bromide had a much darker colour when dry and showed a very sudden decolourisation on passing from 0 to 10% R.H. compared to the composition without bromide.

Example 3

100 grams of humidified gel were soaked for four hours in 200 mls of solutions containing 10% sodium bromide and either 1% or 10% by weight ammonium iron(III) sulphate 12-hydrate. The gels were then dried and examined as in example 1. Compositions 1a and 1j (described above) served as controls with no bromide.

TABLE 5

| | Solution composition | | Composition of dry gel | | Weight ratio |
|---|---|---|---|---|---|
| Composition | % iron alum | % NaBr | % Fe | % Br | Br:Fe |
| 1a | 1 | 0 | 0.06 | 0 | 0 |
| 3a | 1 | 10 | 0.08 | 2.49 | 31.1 |
| 1j | 10 | 0 | 0.20 | 0 | 0 |
| 3b | 10 | 10 | 0.28 | 2.59 | 9.2 |

The indicating gels mentioned in Table 5 were exposed to streams of air at various relative humidities (% R.H.), as described above, and the resulting colours measured and recorded in Table 6 below.

TABLE 6

| Composition | % R.H. | L* | a* | b* | Colour |
|---|---|---|---|---|---|
| 1a | 0 | 47.94 | +4.36 | +27.98 | Orange |
| | 10 | 48.34 | +4.49 | +26.71 | Orange |
| | 20 | 53.10 | +2.73 | +24.52 | Light orange |
| | 40 | 52.41 | +1.48 | +18.82 | Pale orange |
| | 80 | 61.14 | +0.07 | +13.96 | Pale yellow |
| 3a | 0 | 42.92 | +13.56 | +46.89 | Amber |
| | 10 | 43.46 | +9.05 | +46.25 | Orange |
| | 20 | 53.10 | −0.18 | +29.86 | Yellow |
| | 40 | 60.74 | −2.36 | +16.82 | Pale yellow |
| | 80 | 65.21 | −1.59 | +7.78 | Almost colourless |
| 1j | 0 | 46.19 | +9.20 | +41.14 | Orange |
| | 10 | 48.41 | +9.25 | +38.26 | Orange |
| | 20 | 50.12 | +5.96 | +37.94 | Light orange |
| | 40 | 51.38 | +1.57 | +25.68 | Pale orange |
| | 80 | 61.10 | −1.35 | +14.24 | Pale yellow |
| 3b | 0 | 26.06 | +18.12 | +21.33 | Deep brown |
| | 10 | 32.27 | +19.69 | +27.48 | Deep amber |
| | 20 | 47.10 | +8.20 | +42.58 | Orange |

TABLE 6-continued

| Composition | % R.H. | L* | a* | b* | Colour |
|---|---|---|---|---|---|
|  | 40 | 54.27 | +3.12 | +35.43 | Light orange |
|  | 80 | 64.81 | −2.41 | +26.90 | Pale yellow |

Once again, the colour of the bromide-containing gel when dry is much deeper than the colour of the corresponding gel without bromide. In the case of the bromide-containing gel with the lower iron content the tendency for the colour to fade rapidly is particularly evident as the a* value falls swiftly on passing from 0 to 10 to 20% R.H. As observed in example 1, the bromide-containing gel with an iron content higher than about 0.2% (example 3b above) begins to change colour only above 10% R.H. but when it does so it is rapid and dramatic.

Example 4

Example 2 was repeated but using sodium bromide in place of magnesium bromide, and about 10 mls of water rather than 5 ml on account of the lower solubility of the sodium salt. Table 7 below gives the compositions of the dry gels as determined by analysis. They all had similar iron contents but covered a range of bromide contents.

TABLE 7

| Composition | % Fe | % Br | Weight ratio Br:Fe |
|---|---|---|---|
| 4a | 0.25 | 0 | 0 |
| 4b | 0.22 | 0.44 | 2.0 |
| 4c | 0.23 | 1.74 | 7.6 |
| 4d | 0.21 | 2.69 | 12.8 |

The indicating gels in Table 7 were exposed to streams of air at various relative humidities (% R.H.), as described above, and the resulting colours measured and recorded below in Table 8.

TABLE 8

| Composition | % R.H. | L* | a* | b* | Colour |
|---|---|---|---|---|---|
| 4a | 0 | 52.22 | +4.55 | +36.36 | Orange |
|  | 10 | 52.39 | +2.85 | +33.74 | Light orange |
|  | 20 | 53.40 | +1.64 | +26.96 | Yellow |
|  | 40 | 59.20 | −0.88 | +14.73 | Pale yellow |
|  | 80 | 61.70 | −1.74 | +11.06 | Pale yellow |
| 4b | 0 | 44.72 | +28.42 | +43.38 | Deep orange |
|  | 10 | 58.66 | +2.41 | +49.50 | Light orange |
|  | 20 | 72.66 | −0.04 | +52.10 | Yellow |
|  | 40 | 77.14 | −2.28 | +28.63 | Pale yellow |
|  | 80 | 82.26 | −3.96 | +23.68 | v. pale yellow |
| 4c | 0 | 33.34 | +27.56 | +29.60 | Deep reddish amber |
|  | 10 | 48.68 | +20.36 | +48.09 | Deep orange |
|  | 20 | 68.78 | +4.07 | +60.30 | Orange |
|  | 40 | 74.04 | −2.45 | +41.15 | Yellow |
|  | 80 | 78.30 | −5.48 | +39.34 | Yellow |
| 4d | 0 | 29.21 | +25.60 | +23.60 | Reddish brown |
|  | 10 | 41.77 | +21.18 | +40.54 | Deep orange |
|  | 20 | 63.66 | +9.10 | +63.19 | Orange |
|  | 40 | 72.42 | −0.57 | +49.53 | Yellow |
|  | 80 | 76.64 | −3.96 | +49.86 | Yellow |

As observed before for gels with iron contents greater than approximately 0.2% examples 4c and 4d above do not begin to decolourise until after a relative humidity of 10% has been achieved. This effect is, however, also influenced by the Br:Fe ratio. 4b, with a low Br:Fe ratio (2.0) decolourises rapidly, and mostly below 10% R.H. Example 4c, with a higher Br:Fe ratio (7.6), begins decolourising at 10% R.H. and has almost completely changed colour at 20% R.H. Example 4d, with the highest Br:Fe ratio (12.8), also begins decolourising at 10% R.H. but still has an appreciable a* component at 20% R.H. It is fully decolourised at 40% R.H. For a given iron content, the relative humidity at which the colour change occurs can therefore be influenced to some extent by modifying the Br:Fe ratio.

The invention claimed is:

1. An indicating desiccant for indicating humidity at a relative humidity below 20% by a color change comprising a silica-based material provided with, as the active indicator system, a source of iron and a source of bromide, wherein the desiccant is essentially copper-free, or when copper is present it is in an amount which is less than 0.002% by weight with respect to the anhydrous silica-based material.

2. A desiccant as claimed in claim 1 in which the source of iron is present in an amount up to 2.0% by weight, calculated as Fe with respect to weight of the anhydrous silica-based material.

3. A desiccant as claimed in claim 1 in which the source of iron is present in an amount of up to 1.0% by weight, calculated as Fe with respect to weight of the anhydrous silica-based material.

4. A desiccant as claimed in claim 1 in which the source of iron is present in an amount of up to 0.6% by weight, calculated as Fe with respect to weight of the anhydrous silica-based material.

5. A desiccant as claimed in claim 1 in which the source of iron is present in an amount of up to 0.45% by weight, calculated as Fe with respect to weight of the anhydrous silica-based material.

6. A desiccant as claimed in claim 1 in which the source of iron is present in an amount of at least 0.01% by weight, calculated as Fe with respect to weight of the anhydrous silica-based material.

7. A desiccant as claimed in claim 1 in which the source of iron is present in an amount of at least 0.02% by weight, calculated as Fe with respect to weight of the anhydrous silica-based material.

8. A desiccant as claimed in claim 1 in which the source of iron is present in an amount of 0.02 to 1.0% by weight, calculated as Fe with respect to weight of the anhydrous silica-based material.

9. A desiccant as claimed in claim 1 in which the source of iron is present in an amount of 0.05 to 0.3% by weight, calculated as Fe with respect to weight of the anhydrous silica-based material.

10. A desiccant as claimed in claim 1 in which the bromine content is equal to, or greater than, the amount of iron.

11. A desiccant as claimed in claim 1 in which the source of bromide is present in an amount such that the weight ratio of Br to Fe is at least 0.1:1.

12. A desiccant as claimed in claim 1 in which the source of bromide is present in an amount such that the weight ratio of Br to Fe is at least 0.5:1.

13. A desiccant as claimed in claim 1 in which the source of bromide is present in an amount such that the weight ratio of Br to Fe is at least 1:1.

14. A desiccant as claimed in claim 1 in which the source of bromide is present in an amount such that the weight ratio of Br to Fe is up to 100:1.

15. A desiccant as claimed in claim 1 in which the source of bromide is present in an amount such that the weight ratio of Br to Fe is up to 50:1.

16. A desiccant as claimed in claim 1 in which the source of bromide is present in an amount such that the weight ratio of Br to Fe is up to 20:1.

17. A desiccant as claimed in claim 1 in which the bromide source comprises a water soluble salt.

18. A desiccant as claimed in claim 1 in which the bromide source is selected from one or more of the group consisting of alkali metal bromides, alkaline earth metal bromides, transition metal bromides and ammonium bromide.

19. A desiccant as claimed in claim 1 in which the bromide source is selected from one or more of the group consisting of sodium bromide, potassium bromide, calcium bromide, magnesium bromide, zinc bromide and ammonium bromide.

20. A desiccant as claimed in claim 1 in which the source of iron is an iron (III) salt or salts.

21. An indicating desiccant for indicating humidity at a relative humidity below 20% by a color change comprising a silica-based material provided with, as the active indicator system, a source of iron and a source of bromide, wherein the desiccant is essentially copper-free, or when copper is present it is in an amount which is less than 0.002% by weight with respect to the anhydrous silica-based material, in which the iron source is provided by one or more salts selected from the group consisting of iron(II) sulphate, iron(III) chloride, iron (III) nitrate, iron(III) sulphate, ammonium iron(II) sulphate, ammonium iron(III) sulphate and potassium iron(III) sulphate.

22. A desiccant as claimed in claim 1 in which the silica-based material is silica gel.

23. A desiccant as claimed in claim 22 in which the silica gel is a beaded silica gel.

24. A desiccant as claimed in claim 22 in which the silica gel is a granular silica gel.

25. A desiccant as claimed in claim 22 in which the silica gel is a dry or humidified gel.

26. A desiccant as claimed in claim 22 in which the silica gel has a pore volume to nitrogen in the range 0.2 to 2.0 $cm^3 g^{-1}$ and a BET surface area in the range 200 to 1500 $m^2 g^{-1}$.

27. A method of preparing an indicating desiccant comprising impregnating a silica-based material with a source of iron and a source of bromide to produce an essentially copper-free product in which the iron and bromide are the active indicators.

28. A method as claimed in claim 27 in which the source of iron is present in an amount up to 2.0 percent by weight, calculated as Fe with respect to weight of the anhydrous silica-based material, and the source of bromide in an amount such that the weight ratio of Br to Fe is at least 0.1:1.

29. A method as claimed in claim 27 in which a humidified silica gel containing from 20 to 30% by weight water is soaked in a solution containing from 0.1% to the saturation point of an iron salt and a source of bromide, excess solution is drained from the treated silica gel and the silica gel is dried at a temperature in the range 80° C. to 230° C.

30. A method as claimed in claim 29 in which the gel is soaked in said solution for a period in the range of 2 to 24 hours.

31. A method as claimed in claim 28 in which impregnation is effected by mixing a humidified silica gel containing from 15 to 30 percent moisture by weight with a solution containing a source of iron and a source of bromide, the amount of solution used being just sufficient to produce the required loading of iron and bromide on the silica gel, and subsequently drying the treated silica gel at a temperature in the range 80° C. to 230° C.

32. A desiccant as claimed in claim 1, wherein the desiccant is essentially copper-free.

33. The desiccant as claimed in claim 1, wherein copper is present in an amount less than 0.002% by weight with respect to the anhydrous silica-based material.

* * * * *